United States Patent [19]

Crowley

[11] Patent Number: 5,544,660
[45] Date of Patent: Aug. 13, 1996

[54] ACOUSTIC IMAGING CATHETER AND METHOD OF OPERATION

[75] Inventor: Robert J. Crowley, Wayland, Mass.

[73] Assignee: Boston Scientific Corp., Natick, Mass.

[21] Appl. No.: 413,373

[22] Filed: Mar. 30, 1995

[51] Int. Cl.⁶ ..................................................... A61B 8/12
[52] U.S. Cl. ..................................................... 128/662.06
[58] Field of Search .................. 128/660.01, 662.03, 128/662.06; 73/607, 625, 626

[56] References Cited

U.S. PATENT DOCUMENTS

| | | | |
|---|---|---|---|
| 4,726,230 | 2/1988 | Yoshikawa et al. | 128/661.01 |
| 4,811,740 | 3/1989 | Ikeda et al. | 128/660.01 |
| 5,318,027 | 6/1994 | Fukui | 128/660.01 |
| 5,351,693 | 10/1994 | Taimisto et al. | 128/662.06 |
| 5,353,797 | 10/1994 | Matsushima et al. | 128/661.01 |

*Primary Examiner*—George Manuel

[57] ABSTRACT

An acoustical imaging catheter adapted to be used with a drive and control system wherein the system can be automatically advised to compensate for different characteristics of different acoustical imaging catheters used on the drive and control system. The catheter includes an elongated sheath (12) having a proximal end (7) and a distal end. A lumen is disposed within the sheath (12). A drive shaft (18) has an acoustic transducer disposed on the distal end thereof. The drive shaft and the transducer are disposed in the lumen of the sheath. An indicia bearing surface (2) is disposed on the sheath (12). The indicia bearing surface (2) is encoded with identification and characteristics especially related to the catheter and transducer. The indicia bearing surface is adapted to be read by a sensor associated with the control system to enable the control system to compensate for the identification and characteristics of the catheter being used.

9 Claims, 3 Drawing Sheets

ACOUSTIC IMAGING CATHETER AND METHOD OF OPERATION

BACKGROUND OF THE INVENTION

The present invention relates to acoustic imaging catheters employing a rotating transducer. The invention especially relates to acoustic imaging systems employing mechanically scanned ultrasound catheter transducers and the consoles and hardware to drive them. The invention further relates to a method of using acoustic imaging catheters utilizing characteristics individually encoded on the catheter.

DESCRIPTION OF THE PRIOR ART

Ultrasound probe catheters that are proximally connected to a motor drive and an electrical interface device are well known to the art. United States patent to Crowley et al., U.S. Pat. No. 4,951,677, discloses an ultrasound probe of this type. A system utilizing such probes can accommodate a wide variety of catheter types, frequencies and configurations. Also, individual catheters within a type each have differences which are characteristic to the particular catheter being used. I have found that not only must the details of the catheter type be noted but also the individual differences must be noted and compensated for if the information generated by the probe is to have validity. Console adjustments have to be made for variables such as image size, gain, frequency, rate of rotation and transmission power which are typically unique to a particular type, function or size of catheter and currently the operator must manually input specific data as to type and characteristics in order to obtain the desired image quality. Delays and possibilities of mistakes can be made when inputting such data. Moreover, the image settings in part are subject to an operator's expertise which can vary. Additionally, governmental limits on acoustic power outputs must be controlled and limited for specific frequencies catheter types and applications. Assurances that these settings are consistently accurately established for each catheter is desirable.

Ordinarily, external ultrasound probes include a motor, a rotary transformer, a cable to a console, a readable eprom daisy chain or multi-pin diode array or other means to encode operating data needed to operate the console. Catheter ultrasound probes, however, do not have an integral motor and cable to the console. They are connected to a motor unit that in turn is connected to the console. A uniform mechanical and electrical interface must be made between the motor and the catheter. Also, the catheter must be a single use disposable design of low cost so the addition of diodes, eproms, daisy chains or other hardware is prohibitively expensive, bulky or not flexible enough to encompass the large range of expected varieties of catheters.

SUMMARY OF THE INVENTION

Thus the primary object of the present invention is an inexpensive alternative to the various types of probe recognition requirements that is reliable and translatable to the console.

According to the present invention, a motor driver is equipped with a LED on the periphery of its rotor. The LED is connected through the motor to a photodetector which is arranged with a light pipe so that light from the LED can be reflected from an opposing surface into a photo detector. The leads of the photodetector are brought through the motor and to a console. A motor cover is disposed in close proximity to a rotary transformer with a diode and detector assembly. A transparent window is provided in the cover and is arranged in an arc corresponding with the path of rotation and radius of the diode detector assembly. In the preferred embodiment of the invention, the ultrasonic imaging catheter is of conventional design as shown in the above-mentioned Crowley et al. patent. A flared skirt or other readable surface is disposed at the proximal end of the catheter as an extension from a boot and serves as its base. Data relating to each catheter, for example, its type, size and use, is recorded on an indicia bearing surface disposed on the catheter. Also recorded can be characteristics of the catheter that are specific to itself. For example the frequency, band width, pulse length, reverberation, required transient voltage, thermal impedance, and required motor scan speed can be recorded on the surface. Thus, data that previously was required to be either entered into the console itself or had to be calibrated before use of the catheter can be encoded on the catheter itself thus eliminating these data entry steps and double calibration.

The acoustical imaging catheter of the present invention is used with a drive and control system wherein the system can be advised on how to compensate for differences between different acoustical imaging catheters used on the drive and control system. The catheter includes an elongated sheath with a proximal and a distal end. A lumen is disposed in the sheath and a drive shaft having a proximal and a distal end is disposed in the lumen. An acoustic transducer is disposed on the distal end of the drive shaft and the drive shaft and transducer are disposed in the lumen. An indicia bearing surface is disposed on the sheath. The surface is encoded with characteristics and information especially related to the catheter. The surface is adapted to be read by a sensor associated with the control system to enable the control system to compensate for the individual characteristics of the transducer being used.

Additionally the invention relates to a method of using an acoustical imaging catheter in which a catheter is identified for use in a medical procedure. The characteristics of said catheter are measured and these characteristics are encoded on the catheter at a location suitable for scanning by a drive and control system adapted to be associated with said catheter. The encoded catheter is placed on to the drive and control system and the encoded characteristics are read into the control system. The control system is adjusted to compensate for the encoded characteristics automatically by its reading of the encoded data.

DESCRIPTION OF THE PREFERRED EMBODIMENTS

Figure 1:
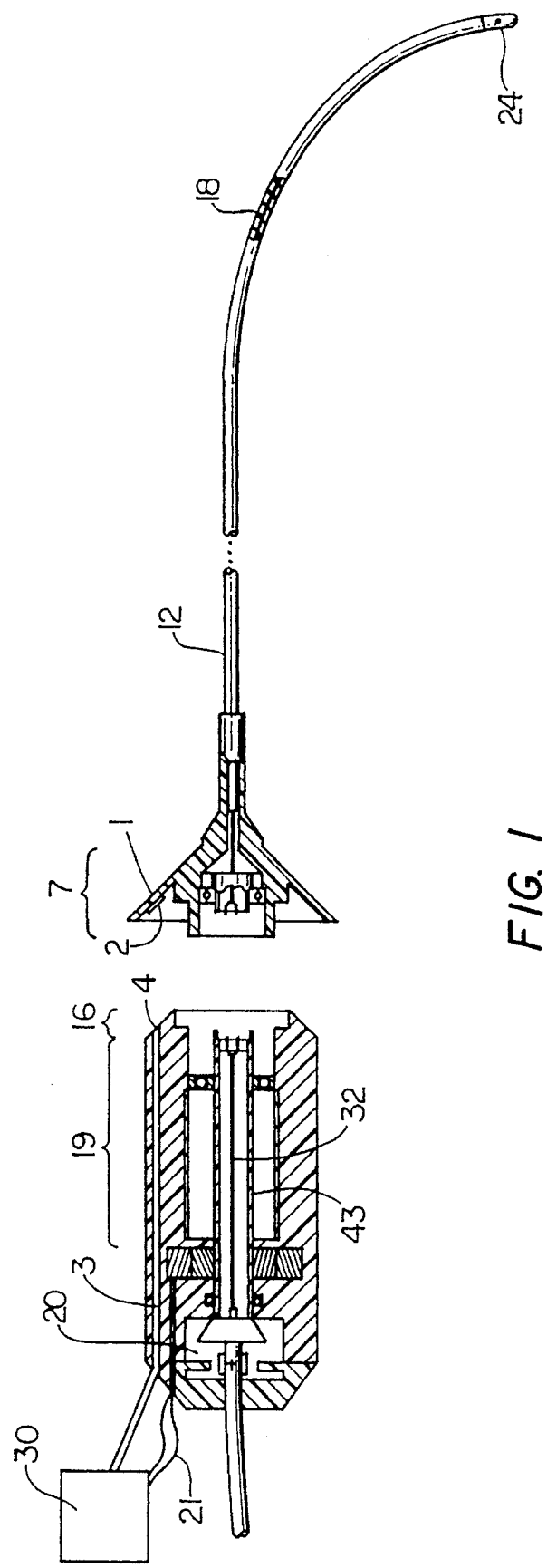
FIG. 1 is a cross-sectional view of a motor connector assembly to which a catheter is connected.

The catheter is adapted to be positioned in the body by standard catheter procedures such as within a blood vessel or the heart by guiding the flexible catheter through various blood vessels along a certain circuitous path. For example the catheter can be introduced percutaneously with an introduction sheath disposed in a perforation in the femoral artery.

Micro acoustic imaging catheters according to the present invention are driven and monitored by a controller and drive system 30. The catheter is comprised of a disposable catheter sheath 12 having an acoustically transparent window 24 at its distal end. The sheath 12 surrounds a miniature rotatable ultrasonic transducer, as is well known, driven by a special hi-fidelity flexible drive shaft 18. A mating connector 7 is disposed at the proximal end of the catheter and is adapted to be associated with a console and control-drive system 30.

The disposable catheter sheath 12 is a long tube extruded from standard catheter materials. The transducer cover 24 is disposed at the distal end of the sheath 12. The cover 24 is constructed of a material that is transparent to sound waves such as high impact polystyrene. The cover 24 has a thickness of approximately 0.125 mm and a length of about 8 mm.

The transducer is disposed within the catheter sheath 12 and under the cover 24. It is formed in a known manner with a ceramic material such as barium titanates, lead zirconium titanates, lead metaniobates. These materials are capable of transforming pressure distortions on a surface to electrical voltage and vice versa. The transducer assembly is further provided with an acoustic lens having a radius of curvature that is greater than about 2.5 mm and provides a focus over a predetermined range. The lens is positioned at an acute angle to the longitudinal axis of the catheter so that during rotation it scans a conical surface from the transducer tip. The transducer backing is acoustically matched to the transducer element to improve axial resolution.

Figures 2, 3:
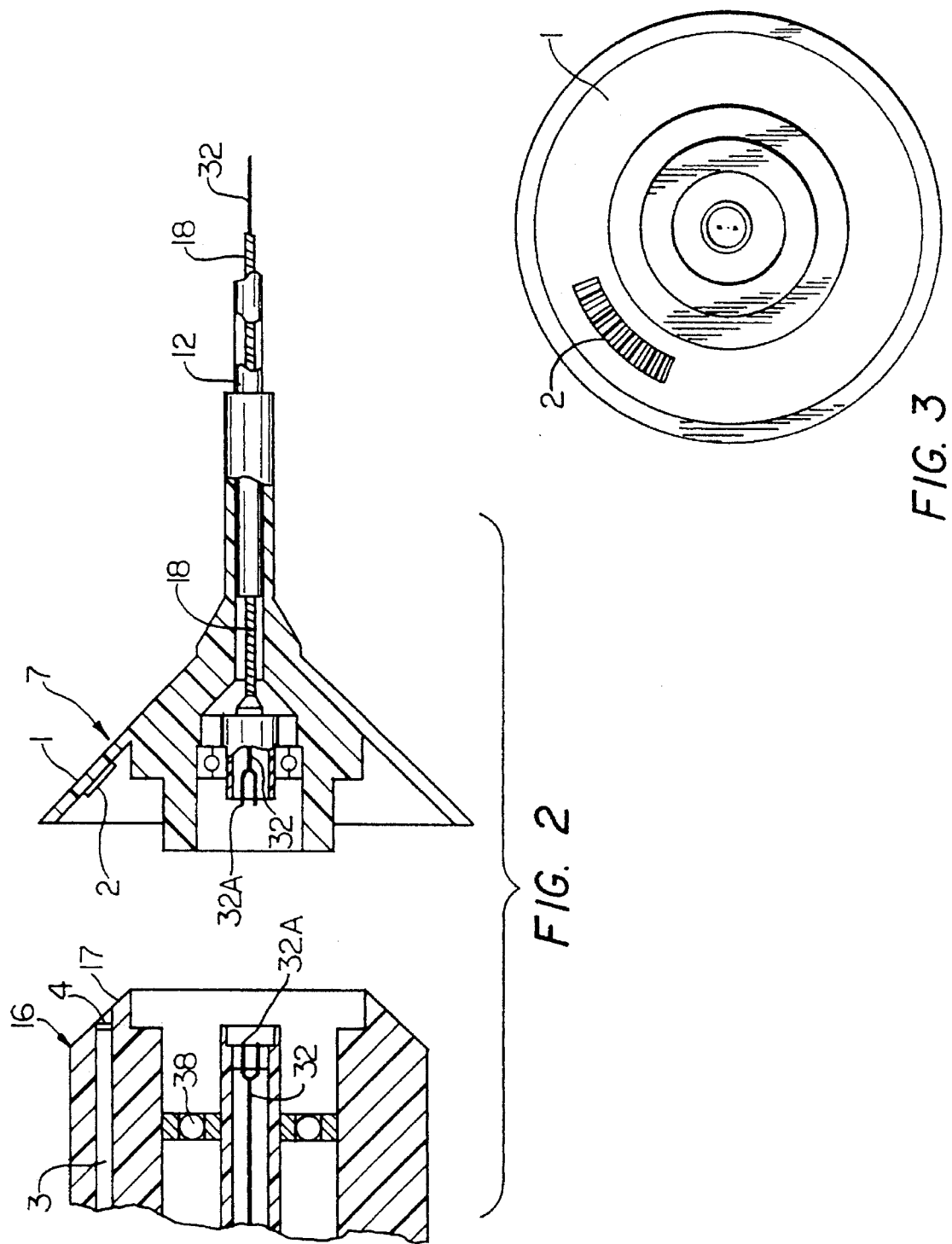
FIG. 2 is an enlarged view of the assembly shown in FIG. 1.
FIG. 3 is an elevational view of the proximal end of the catheter.

As shown in FIGS. 1 and 2, the connector 7 is disposed at the proximal end of the sheath 12. It is adapted to be associated with a connector 16 housing the driving motor 20. Electric wires 21 extend into a center shaft 43 of the driving motor 20. Wires 21 emerge as coaxial cable 32. The center shaft 43 and connector 16 rotate together as do the cable 32 that pass through them. In the enlarged view of FIG. 2 it can be seen how the motor connector 16 and the drive shaft connector 7 mate so when the two assemblies are pushed together, they make both electrical and mechanical connection. The catheter connection is held in position by ball bearings 38 which provide a thrusting surface for rotating connector 7 and drive shaft 18 which rotates the transducer at speeds of about 1800 r.p.m. The transducer is electrically connected to components 30 by the coaxial cable 32 that extends through coil assembly 18 into the motor 20. It is then connected to the components 30 by wires 20 which send receive and interpret signals from the transducer. A conventional electrical connector 32A is disposed in the cable 32 to enable the drive shaft assembly 18 to be electrically connected through the drive motor 18 to the components 30. Components 30 include an LED reader and can include a cathode ray tube, electronic controls for the rotary repetition rate and standard ultrasonic imaging equipment. A rotation detector in the form of a shaft encoder detects the instantaneous rotational position of the proximal rotating assembly and applies the positional information to the electronic components for use in producing a scanning image.

The cathode connector includes a boot which can have a generally conical external shape in the form of a flared skirt 1. An indicia bearing surface 2 is disposed inside of the flared skirt 1. The surface 2 is imprinted with shapes normally read by automatic equipment such as bar lines or other readable indicia. The indicia bearing surface 2 matches with a LED reader that is one of the components 30. The component 30 is connected to a light pipe 4 that is housed within a conduit 3 fitted in the thrusting surface 16 of the connector. Light pipe 4 emerges through a surface 17. After placing the connector 7 on the thrusting surface 16, the LED will scan the indicia on indicia bearing surface 2 to identify the parameters that have to be registered for interpretation of the particular catheter being used.

As shown in FIG. 3, indicia is encoded on the surface 2 disposed on flared skirt 1 of the connector 7.

Figure 4:
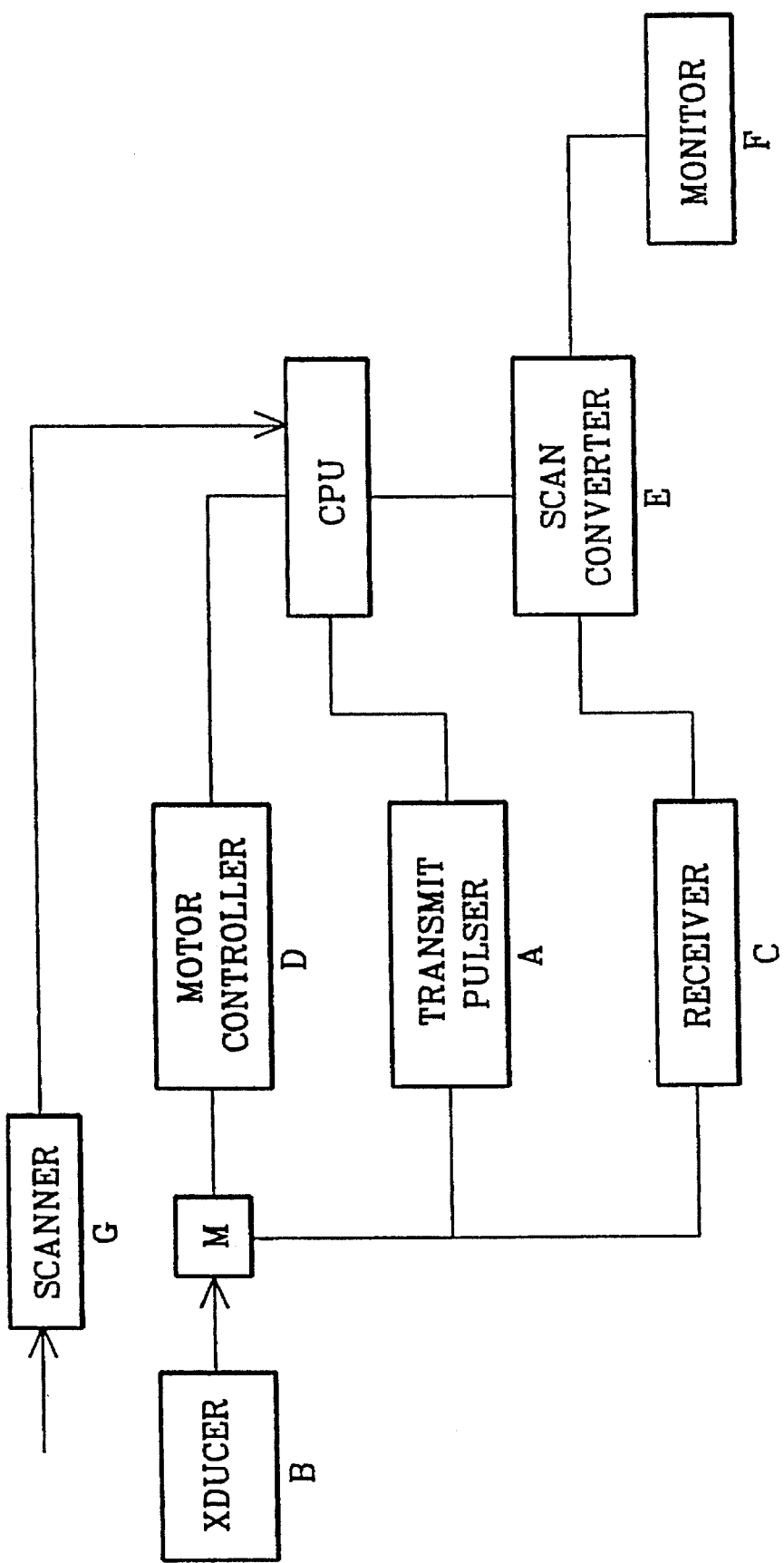
FIG. 4 is a block diagram of the electronic components useful with the acoustical catheter of the present invention.

Referring to FIG. 4 a block diagram of the electronics of the basic analog ultrasound imaging system used with an acoustical catheter is shown. The motor controller D positions the transducer B for the next scan line. The transmit pulsar A drives the ultrasound transducer. The transducer B converts the electrical energy into acoustical energy in a emits a sound wave. The sound wave reflects off various interfaces in the region of interest and a portion returns to the transducer. The transducer converts the acoustic energy back into electrical energy. The scanner G reads the encoded material on the indicia bearing surface of the catheter and transmits the results to the computer which adjusts itself to operate the transducer in accordance with its instructions.

While it is apparent that changes and modifications can be made within the spirit and scope of the present invention, it is my intention, however, only to be limited by the appended claims.

As my invention I claim:

1. An acoustical imaging catheter adapted to be used with a drive and control system wherein the system can be advised to compensate for different characteristics of different acoustical imaging catheters used on said drive and control system, said catheter comprising:

an elongated sheath having a proximal and a distal end, said sheath having a lumen therein;

a drive shaft having a proximal and a distal end and an acoustic transducer disposed on the distal end of said drive shaft, said drive shaft and said transducer being disposed in the lumen of said sheath;

indicia means disposed on said sheath, said indicia means being encoded with characteristics and identification especially related to said catheter and transducer, said indicia means being disposed to be read by a sensor associated with said control system to enable said control system to compensate for the individual characteristics and identification of the catheter and transducer being used.

2. The catheter according to claim 1 further including coupling means disposed on said proximal end, said coupling means including a flared skirt extending therefrom, said indicia means including optically readable indicia disposed on the inner surface thereof.

3. The catheter according to claim 1 wherein the identification encoded on said indicia means includes data specific to the catheter including type, size and use.

4. The catheter according to claim 3 wherein the characteristics encoded on said indicia means further includes characteristics specific to the individual catheter comprising its frequency, band width, pulse length, reverberation, required transient voltage, thermal impedance, and required motor scan speed.

5. A catheter adapted to be used in a medical procedure together with a system to provide medical diagnoses, said catheter having specific characteristics which distinguishes it from other catheters wherein the system can be advised as to which catheter is being used and what to compensate for to accommodate differences between the catheter being used and such similar catheters, said catheter comprising:

an elongated sheath having a proximal and a distal end, said sheath having a lumen therein;

means inside said lumen to provide a medical test;

indicia means disposed on said sheath, said indicia means being encoded with characteristics and information especially related to said catheter, said indicia means being disposed to be read by a sensor associated with said control system to enable said control system to compensate for the individual characteristics of the transducer being used.

6. A method of using an acoustical imaging catheter, said method comprising:

identifying an acoustical imaging catheter employing a rotating transducer to be used in a medical procedure;

measuring characteristics of said catheter;

encoding the identification and characteristics of said catheter on said catheter at a location suitable for scanning by a drive and control system adapted to be associated with said catheter;

placing said encoded catheter onto said drive and control system and reading the encoded identification and characteristics into the control system;

adjusting said control system to compensate for the encoded identification and characteristics on said catheter;

using said catheter in a medical procedure utilizing said control system which has been adjusted for said encoded identification and characteristics.

7. The method according to claim 6 wherein the encoded identification includes data specific to each catheter including type, size and use.

8. The catheter according to claim 7 wherein the encoded characteristics comprises frequency, band width, pulse length, reverberation, required transient voltage, thermal impedance, and required motor scan speed.

9. The method according to claim 6 wherein the step of reading includes optically scanning the encoded identification and characteristics through a light pipe disposed within said drive and control system.

\* \* \* \* \*